(12) United States Patent
Lei et al.

(10) Patent No.: US 11,099,183 B2
(45) Date of Patent: Aug. 24, 2021

(54) APPARATUS FOR COLLECTING AND DETECTING AN ANALYTE IN A FLUID SAMPLE

(71) Applicants: Healgen Scientific Limited, Houston, TX (US); Zhejiang Orient Gene Biotech Co., LTD, AnJi (CN)

(72) Inventors: Siyu Lei, AnJi (CN); Jianqiu Fang, Houston, TX (US); Lili Shen, AnJi (CN)

(73) Assignees: Zhejiang Orient Gene Biotech Co., Ltd., Zhejiang (CN); Healgen Scientific Limited, Houston, TX (US)

( * ) Notice: Subject to any disclaimer, the term of this patent is extended or adjusted under 35 U.S.C. 154(b) by 334 days.

(21) Appl. No.: 16/048,660

(22) Filed: Jul. 30, 2018

(65) Prior Publication Data
US 2019/0339263 A1 Nov. 7, 2019

(30) Foreign Application Priority Data
May 3, 2018 (CN) .......................... 201820648661.9

(51) Int. Cl.
*G01N 1/00* (2006.01)
*G01N 33/543* (2006.01)
*G01N 33/94* (2006.01)

(52) U.S. Cl.
CPC ..... *G01N 33/54366* (2013.01); *G01N 33/946* (2013.01)

(58) Field of Classification Search
None
See application file for complete search history.

(56) References Cited

U.S. PATENT DOCUMENTS 5,352,410 A * 10/1994 Hansen ................ A61B 10/007
422/419

* cited by examiner

*Primary Examiner* — Jyoti Nagpaul
(74) *Attorney, Agent, or Firm* — NZ Carr Law Office

(57) ABSTRACT

The present invention provides an apparatus for detecting an analyte in a fluid sample, comprising a fluid sample collection element, comprising a fluid sample collection element that comprises an absorbing element; a carrier for accommodating a testing element; and a chamber for accommodating a testing element carrier, wherein the testing element carrier is located in the chamber, and the carrier further comprises an extrusion structure that is in contact with the absorbing element and extrudes the absorbing element.

15 Claims, 8 Drawing Sheets

APPARATUS FOR COLLECTING AND DETECTING AN ANALYTE IN A FLUID SAMPLE

RELATED APPLICATIONS

This application claims priority to Chinese Patent Application No. 201820648661.9, filed on May 3, 2018, which is herein incorporated by reference in its entirety.

FIELD OF THE INVENTION

The present invention relates to an apparatus and a method for detecting an analyte in a fluid sample, and in particular, to an apparatus and method for collecting saliva and detecting an analyte in a saliva sample.

BACKGROUND

The following background art is provided to assist readers in understanding the present invention rather than a prior art.

At present, illegal drug abuse has become a recognized and increasingly worsening social problem. In 2003, the survey conducted by the US Department of Health and Human Services revealed that about 19.5 million Americans or 8.2% of people over the age of 12 are taking illegal drugs. "Recent use of illegal drugs" refers to the use of an illegal drug within one month before the US Department of Health and Human Services conducted a survey. *Cannabis* is found to be the most commonly used illegal drugs, accounting for 6.2% (14.6 million). Now about 2.30 million people (1.0%) are using cocaine, 604,000 people use Crack, and 1 million people are using hallucinogens, and it is estimated that 119,000 people are using heroin.

In order to fight against the drug abuse and monitor this social problem, the drug testing has become a standard test procedure in various industries such as hiring, education, sports, and law enforcement, etc. To promote this standard testing procedure, the drug testing industry has formed. This industry has provided a wide range of drug testing products. The urine sample collection cup for sample analysis is a classic testing product. These devices may be complex, difficult or dirty for users, or may cause the problem of adulteration in the sample to conceal the use of illegal drugs recently. In addition the urine samples cannot be collected in some cases, for example, on the roadside or in the public places.

Various sample collection and testing apparatuses for clinical or domestic use are available and described in some literatures. For example, the U.S. Pat. No. 5,376,337 disclosed a saliva sampling apparatus in which in which a piece of filter paper is used to collect saliva from examinee's mouth and deliver saliva to an indicator reagent. The U.S. Pat. Nos. 5,576,009 and 5,352,410 disclosed a syringe-type fluid sampling apparatus respectively. For these apparatuses, after the initial results are obtained, fluid samples collected cannot be stored for subsequent confirmatory testing. Further, for another example, the U.S. Pat. No. 7,927,562 disclosed a saliva collection apparatus, but there are still some drawbacks, for example, when the saliva samples collected by the absorption portion are not enough, the squeezing and releasing is still insufficient, resulting in insufficient samples and failure to complete the testing; or sometimes there are too much liquid partially, causing flooding and unable to obtain correct detection results.

Many other sample collection and testing apparatuses are inefficient in extracting samples from the collection apparatus. Many of these apparatuses are very complex in the design and manufacturing, requiring expensive materials. Therefore, it is necessary to collect and test samples with better method and apparatus.

SUMMARY

In order to solve the existing problems in the prior art, the present invention provides an apparatus for collecting and detecting an analyte in a fluid sample, comprising: a fluid sample collection element that comprises an absorbing element; a testing element carrier; and a chamber for accommodating a testing element carrier, wherein the testing element carrier is located in the chamber.

In some preferred embodiments, the apparatus further comprises an extrusion structure for extruding the absorbing element. In some preferred embodiments, the extrusion structure and the testing element carrier are an integrated structure, or the extrusion structure is located on a testing element carrier. In some preferred embodiments, the extrusion structure cooperates with the absorbing element to compress the absorbing element. In some preferred embodiments, the contact of the extrusion structure with the absorbing element is accomplished by the cooperation of the collection element with the opening of the chamber.

In some preferred embodiments, the extrusion structure comprises a receiving chamber corresponding to the absorbing element, and the receiving chamber is used to receive or carry the absorbing element. In some preferred embodiments, the carrier comprises an inner surface and an outer surface, the outer surface being provided with one or more groove structures, and the groove structure is provided with a testing element. The testing element is a lateral flow test strip. The outer surface of the carrier and the inner surface of the chamber that accommodates the testing element carrier form a separate chamber. In some embodiments, the extrusion structure is located at the bottom of the carrier. In some embodiments, the position of the extrusion structure is higher than the bottom of the chamber that accommodates the testing element carrier. In some embodiments, the testing element carrier comprises a support structure that is located at the bottom of the chamber. In some preferred embodiments, a collection area is formed at the bottom of the chamber that accommodates the testing element carrier, to collect liquid samples that are extruded by the extrusion structure from the carrier.

In some preferred embodiments, the fluid sample collection element comprises an absorbing element for collecting liquid samples and a gripping portion. In preferred embodiments, the gripping portion has a structure that cooperates with an opening of the chamber that accommodates the testing element carrier, by this way, when the fluid sample collection element is inserted into the chamber that accommodates the testing element carrier, the gripping portion cooperates with the opening of the chamber that accommodates the testing element carrier, so that the fluid sample collection element is "retained" in the chamber that accommodates the testing element carrier. In some preferred embodiments, the gripping portion has a matching structure with the opening of the chamber that accommodates the testing element carrier, so that the collection element can be retained in the chamber. In preferred embodiments, the gripping portion has a structure matching with the retaining element such that the fluid sample collection element is retained in a relatively fixed position in the chamber that accommodates the testing element carrier.

In some preferred embodiments, the gripping portion comprises a flexible annular structure that cooperates with the opening of the chamber to seal the opening of the chamber. In some embodiments, the apparatus comprises an inner plug that is connected with the gripping portion. A flexible sheet-like structure is disposed on the inner plug. Here, the "inner plug" refers to the part for entering the chamber or part of the inner plug enters the chamber. Therefore, a flexible sheet-like structure is provided on the inner plug to facilitate sealing of the opening of the chamber; in addition, as the inner plug is connected to the collection element, the collection element can retain the chamber; here the chamber refers to the chamber for accommodating the carrier. In some preferred embodiments, the flexible annular structure is a multi-layer structure, each layer of structure has the property of flexibility. When the absorbing element is inserted into the chamber, the sealing ring cooperates with the opening of the chamber to from a seal. In some preferred embodiments, the flexible annular structure also serves to maintain the collection element in the chamber. The ring is a sheet-like structure that surrounds the gripping portion or the inner plug. The outer diameter of the sealing ring is larger than the inner diameter of the opening of the chamber, so that the sealing ring is deformed to form a sealing structure and retain the collection element in the chamber when the sealing ring is in contact with the inner wall of the opening of the chamber. In some preferred embodiments, the sealing ring is flexible and in the form of a sheet, with a triangular cross-sectional shape. When contacting the inner wall of the chamber, the triangular side is in contact with the inner wall to form a seal, and at the same time, the collection element is retained in the chamber. In some preferred embodiments, the sheet structure has a plurality of layers, or at least 2 layers, or at least 3 layers, at least 4 layers, at least 5 layers. The more the number of layers of flexible sheet structure, the better the sealing effect, and the better the stability of the collection element fixedly retained in the chamber.

Preferably, the gripping portion cooperates with the chamber that accommodates the testing element carrier in a way of locking, fastening, plugging or buckling, so that the fluid sample collection element is retained in the chamber that accommodates the testing element carrier when inserted, or the fluid sample collection element is in a relatively fixed position. The "retain" herein means that the collection element is inserted into the chamber that accommodates the testing element carrier after collecting samples, and under one of the states, the collection element is in a relatively fixed position in the chamber that accommodates the testing element carrier and cannot be inserted any longer.

In some preferred embodiments, the absorbing element is connected to the gripping portion via a rod. Preferably, the collection element, griping portion and connecting rod is an integrated structure.

In some preferred embodiments, the body accommodating the testing element and the chamber for receiving the absorbing element are an integrated structure. The integrated structure can be formed by one-shot injection molding, or can be formed by the body accommodating the testing element and the chamber for receiving the absorbing element through bonding by a laser or a bonding agent.

In some preferred embodiments, the chamber that accommodates the testing element carrier is roughly a structure with elliptical or circular cross-section. The chamber receives the carrier. The other surfaces of the chamber that accommodates the testing element carrier can be transparent or not transparent.

In another aspect, the present invention provides an apparatus for collecting and detecting an analyte in a fluid sample, comprising:

a fluid sample collection element, wherein the fluid sample collection element comprises an absorbing element that absorbs fluid samples and a gripping portion, and a connecting rod that connects the absorbing element and the gripping portion;

a testing element carrier, wherein the testing element carrier comprises a body for carrying a testing element and an extrusion structure for contacting the absorbing element and extruding the absorbing element;

a chamber for accommodating a testing element carrier;

wherein, the gripping portion further comprises a flexible sealing sheet structure, and the sealing sheet structure cooperates with the inner wall of the opening of the chamber that accommodates the testing element carrier, thereby forming an opening for sealing the chamber, and allowing the sample connection element to be retained in the chamber that accommodates the testing element carrier.

In still another aspect, the present invention provides a collection apparatus, comprising an absorbing element that absorbs liquid samples, and a gripping portion. The absorbing element is connected to the gripping portion by a connecting rod, wherein the apparatus further comprises an inner plug body, and one layer or multiple layers of flexible sheet-like structures are provided on the inner plug body.

In some other preferred embodiments, the flexible sheet-like structure has different outer diameter.

In some other preferred embodiments, the flexible sheet-like structure has an acute triangle section.

In some other preferred embodiments, for the two long sides of the acute triangle, one side is perpendicular to the inner plug body 108, and the other side is inclined with the inner plug body.

In some other preferred embodiments, the long side perpendicular to the inner plug is located above the long side inclined with the inner plug body.

In some other preferred embodiments, the outer diameter formed by the inner plug and the flexible sheet-like structure is smaller than the outer diameter of the inner portion.

Beneficial Effect

The apparatus of the present invention can achieve convenient and quick detection and reading of results; in addition, with low production cost, the detection apparatus is more accurate, without causing flooding.

DETAILED DESCRIPTION

Figure 1:
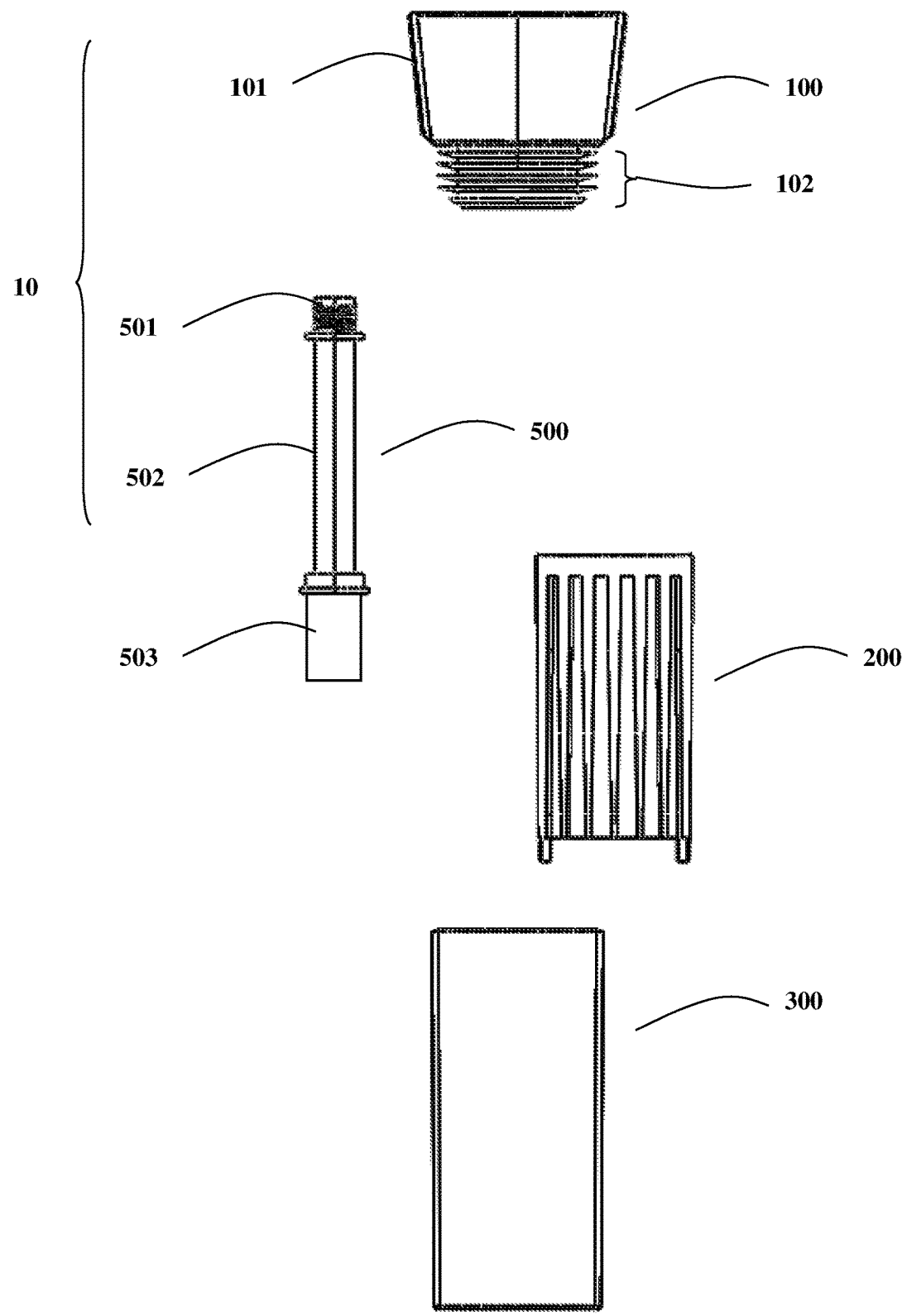
FIG. 1 is a schematic exploded perspective view of a collection and detection apparatus according to an embodiment of the present invention.
Figure 2:
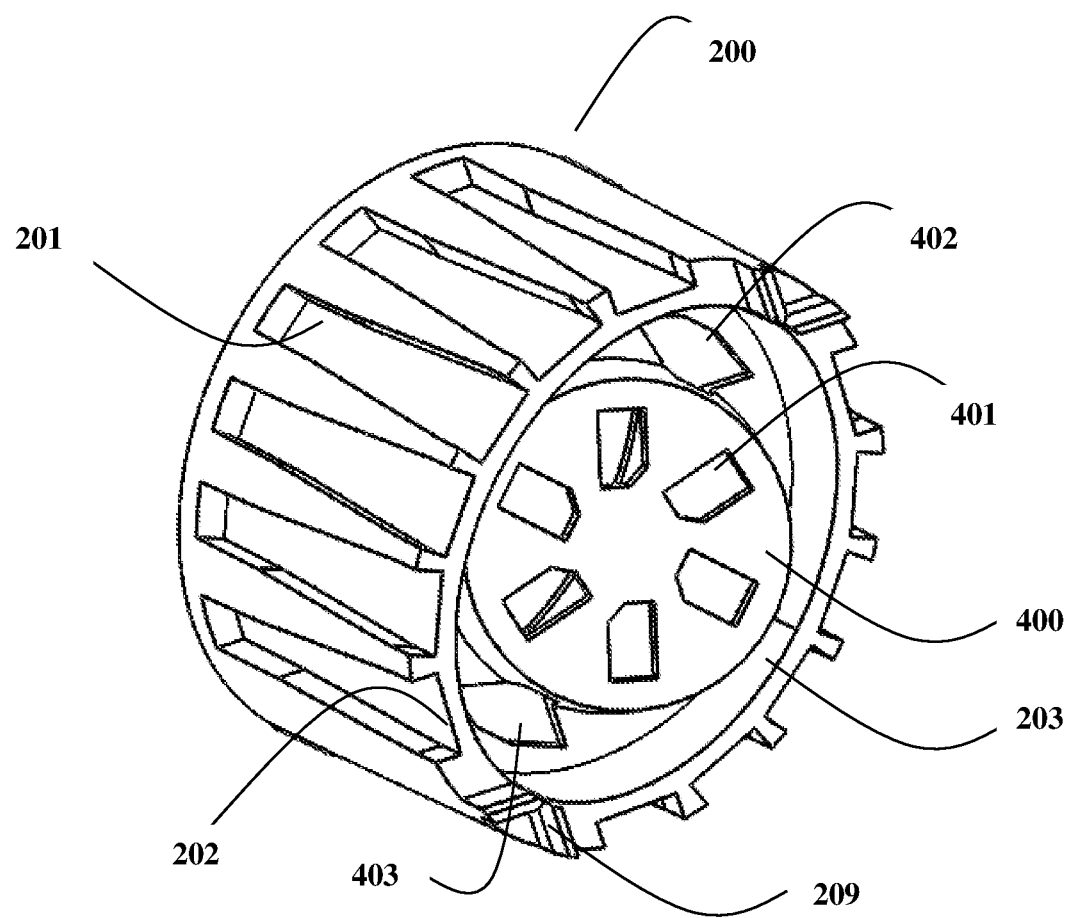
FIG. 2 is a perspective structural view of a carrier for accommodating a testing element according to an embodiment of the present invention.
Figure 3:
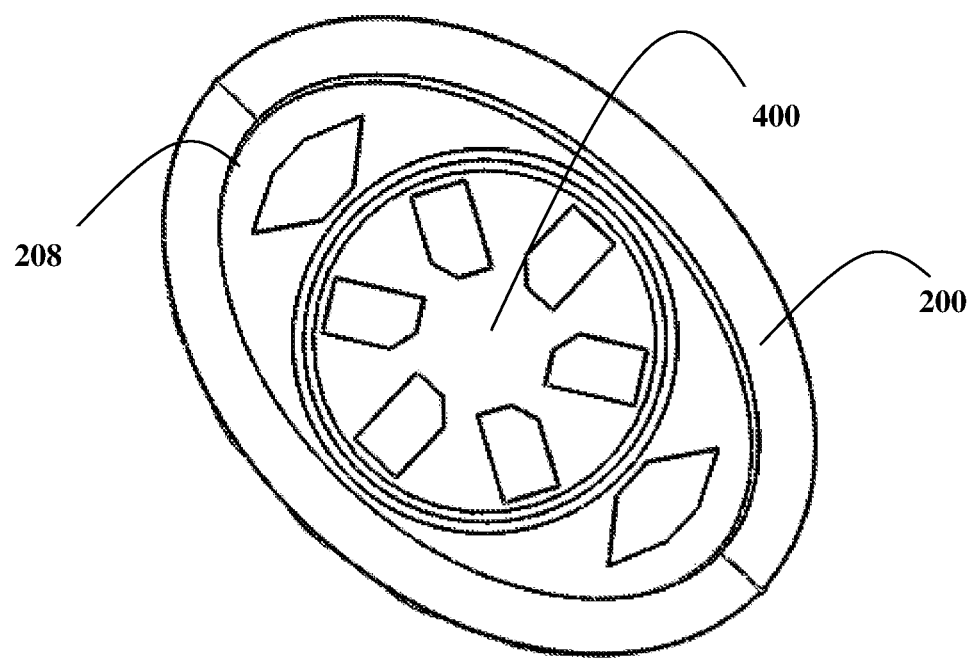
FIG. 3 is a top view of the testing element carrier in FIG. 2.

The structures involved in this invention or the used technical terms are further described below. These descriptions are only to explain how to achieve the ways in this invention through examples, and will not restrict this invention.

Detection

Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, and etc.

Testing Element

Various testing elements can be combined and applied to this invention. The testing element comprises a test strip, which can be analyzed in various forms such as immunoassay or chemical test to detect such analyte in samples as drugs or relevant metabolites indicating physical conditions. In some forms, the test strip is a water absorbent material having sample applying area, reagent area and testing result area. Samples are added to the adding area, and flow to the reagent area under the capillary action. In the reagent area, samples dissolve the reagent and mix with it to detect analyte (if there is analyte in samples). At this time, samples with reagents continue to flow to the testing result area. Other reagents are fixed in the testing result area, and these reagents react and combine with analyte (if there is analyte in samples) or the first type of reagent in the reagent area. In the noncompetitive detection form, if there is analyte in samples, signals will be generated; and if not, signals will not be generated. In the competitive detection form, if there is no analyte in samples, signals will be generated; and if not, signals will not be generated. The invention applies to the testing element of various analytic forms.

When the testing element is a test strip, it can be made from water absorbent or non-water absorbent materials. A test strip can use various materials to transmit liquid, and one material can be superposed on another material. For example, a filter paper can be superposed on the nitrocellulose. Or in the test strip, a region that at least contains one material is located behind the other region that at least contains a different material. In such case, the liquid circulates among regions, and they can be superposed on one another or choose not to superpose. Materials on the test strip can be fixed on (for example) the holder or hard surface of the plastic gasket, to enhance the test strip's sustainable power.

In some embodiments where some detected objects are detected through a signal generation system (for example, at least one enzyme reacts specifically with the detected object), at least one substance generating signals can be absorbed on the analyte detecting area of the test strip, just like being absorbed specifically on the materials of the test strip as described above. In addition, substances generating signals in the sample adding area, reagent area and analyte detecting area of the test strip or all over the whole test strip can be pretreated in advance on one or more materials of the test strip, which can be achieved by adding the solution of substances generating signals to the surface of the application area or soaking one or more materials of the test strip in the signal solution, after which dry the test strip. Moreover, the above method can be used to pretreat substances generating signals in the sample adding area, reagent area and analyte detecting area of the test strip or all over the whole test strip in advance on one or more materials of the test strip. Furthermore, the signal substance existing in the sample adding area, reagent area and detecting area of the test strip can be added to one or more surfaces of the test strip materials as the labeling reagent.

Areas of the test strip can be arranged as follows: a sample adding area, at least a reagent area, at least a testing result area, at least a control area, at least an adulteration detecting area and a liquid absorption area. If the detecting area comprises a control area, the preferred control area is located behind the analyte detecting area of the testing result area. All these areas or their combinations can be on a single test strip containing a material. Additionally, these areas are made from different materials, and are connected together according to the transmission direction of liquid. For example, liquid can be transmitted directly or indirectly among different areas. In this embodiment, different areas can be connected end to end or superposed mutually along the direction of liquid transmission, or connected through other materials such as connecting medium materials (water absorbent materials such as filter paper, glass fiber or nitrocellulose are preferred). By use of the connecting materials, the liquid can flow on materials that connect each area end to end, materials that connect each area end to end but the liquid does not flow, or materials that each area is overlapped mutually (including but not limited to overlapping from end to end) but the liquid does not flow.

If the test strip contains an adulteration detecting control area, the area can be arranged before or after the result detecting area. When the result detecting area contains a control area, the adulteration control area is preferred to be arranged before the control area. In one embodiment of this invention, the test strip is used for analytical judgment and/or control of adulteration. The adulteration control area can be arranged before or after the control area, and preferably, before the control area.

In a specific embodiment of the invention, the testing element or test strip may be located in the testing element carrier 200. Preferably, it is located in the slot 201 of the body of the testing element carrier. In some preferred embodiments, the carrier has two surfaces: an inner surface 208 and an outer surface 205, and the slot 201 is disposed on the outer surface 205. The length of the slot is equivalent to the length of the test strip, so that the sample applying area of the test strip is exposed to the carrier, or partially exposed, by this way, a portion of the sample applying area can be located in the groove 302 at the bottom of the chamber to contact the liquid samples. In some embodiments, there is a plurality of slots on the surface, for example, 1-20 slots, and the analytes detected by the test strips disposed in each slot are different.

Samples

The detection apparatus provided in the invention can be used to detect samples including biological liquid (such as case liquid or clinical samples). The liquid sample or fluid sample can come from solid or semi-solid samples, including excreta, biological tissues and food samples, and these solid or semi-solid samples can be converted to liquid samples by using any suitable methods such as mixing, crushing, macerating, incubating, dissolving or digesting the solid samples in a suitable solution (such as water, phosphate solution or other buffer solutions) with the enzymolysis. "Biological samples" comprise samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is urine; food samples comprise food processed substances, final products, meat, cheese, liquor, milk and drinking water; and plant samples comprise samples from any plants, plant tissues, plant cell cultures and media. "Environmental samples" come from the environment (such as liquid samples coming from lake or other water bodies, sewage samples, soil samples, underground water, sea water and effluent samples), and can also comprise waste water or other sewage water.

Any analyte can be detected by using this invention and a suitable testing element. Preferably, this invention is used to detect the narcotics in the saliva.

Analyte

Examples that can use the analyte related to this invention include some hapten substances, including drugs (such as drug abuse). "Drug abuse" (DOA) means to use drugs (often to paralyze the nerves) for non-medical purposes, which will lead to physical and mental damages, and people who use drugs will be dependent on, addicted to drugs and/or die. Examples of drug abuse include abuse of cocaine, amphetamine AMP (e.g. Black Beauty, white amphetamine tablets, dextroamphetamine, dextroamphetamine tablets, Beans); methylamphetamine MET (crank, meth, crystal, speed); barbiturate BAR (such as Valium, Roche Pharmaceuticals, Nutley, N.J.); sedatives (i.e. sleeping adjuvants); lysergic acid diethylamide (LSD); inhibitors (downers, goofballs, barbs, blue devils, yellow jackets, methaqualone); tricyclic antidepressants (TCA, i.e. imipramine, amitriptyline and doxepin); methylene dioxymetham-phetamine MDMA; phencyclidine (PCP); tetrahydrocannabinol (THC, pot, dope, hash, weed and etc.); opiates (i.e. morphine MOP or opium, cocaine COC, heroin, OXY); antianxiety drugs and sedative hypnotics, the antianxiety drugs are drugs mainly used to relieve anxiety, tension, fear and stabilize emotions, having the function of hypnosis and sedation, including BZO (benzodiazepines), atypical BZ, fused dinitrogen NB23C, benzodiazepines, ligand of BZ receptors, open-loop BZ, diphenylmethane derivatives, piperazine carboxylate, piperidine carboxylate, quinazolinones, thiazines and thiazole derivatives, other heterocyclic, imidazole sedatives/painkillers (such as OXY, MTD), propanediol derivatives-carbamates, aliphatic compounds, anthracene derivatives and etc. The detection apparatus provided in this invention can also be used to detect medicines that are easy to overdose for the medical purpose, such as tricyclic antidepressants (imipramine or analogues) and acetaminophen. These medicines will be resolved into different micromolecular substances after being absorbed by human body, and these micromolecular substances will exist in blood, urine, saliva, sweat and other body fluids or in some of the body fluids.

The analyte detected by this invention includes but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *Staphylococcus, Salmonella, Fusobacterium, Campylobacter, L. monocytogenes, vibrio* or *Bacillus cereus*) and substances relevant with the physiological features in the urine sample, such as pH and specific gravity. For any other clinical urine chemical analysis, the detection can be made by combining the lateral cross flow detection form and the apparatus provided in this invention.

Sample Collection Element

Figure 6:
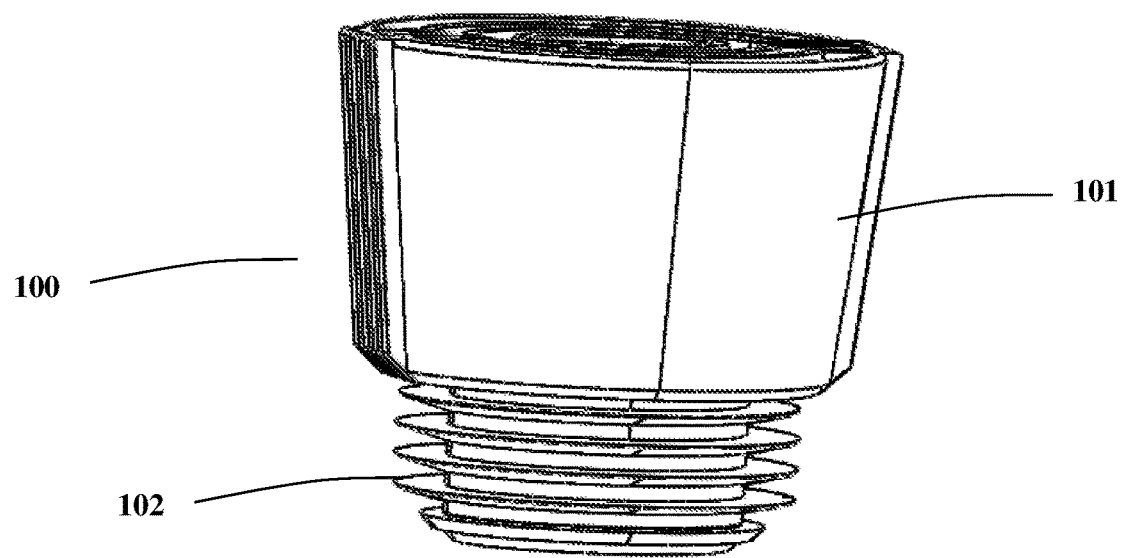
FIG. 6 is a schematic perspective view of a gripping portion of a collection element.
Figure 7:
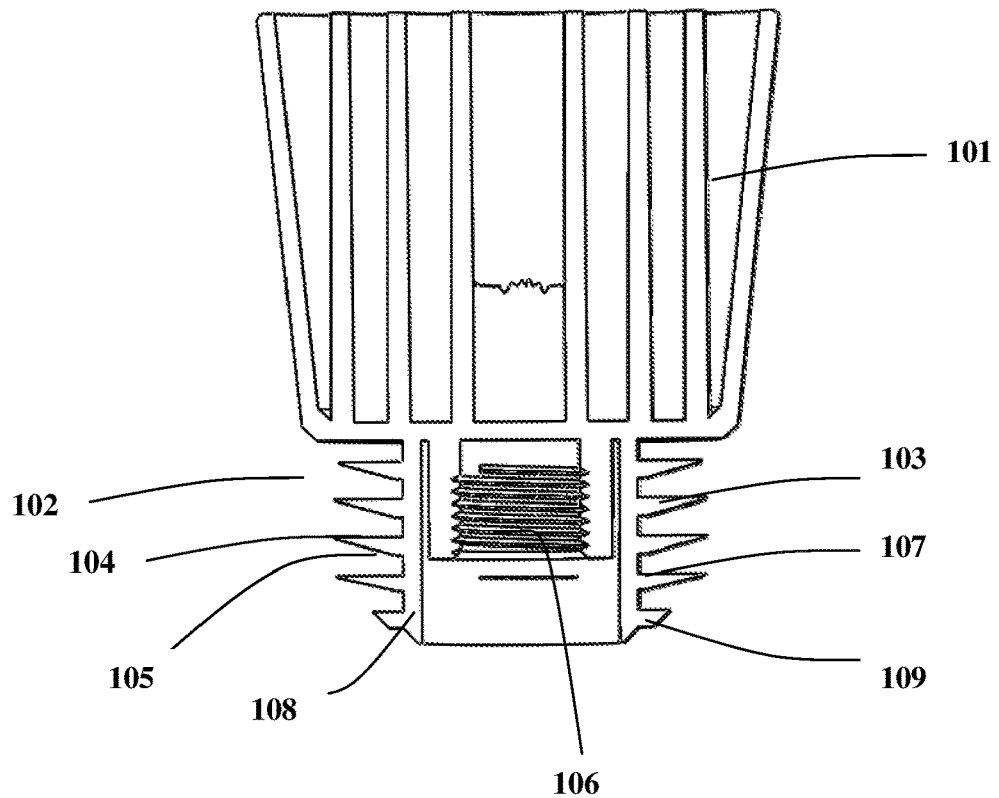
FIG. 7 is a schematic longitudinal sectional view of a gripping portion of a collection element.
Figure 8:
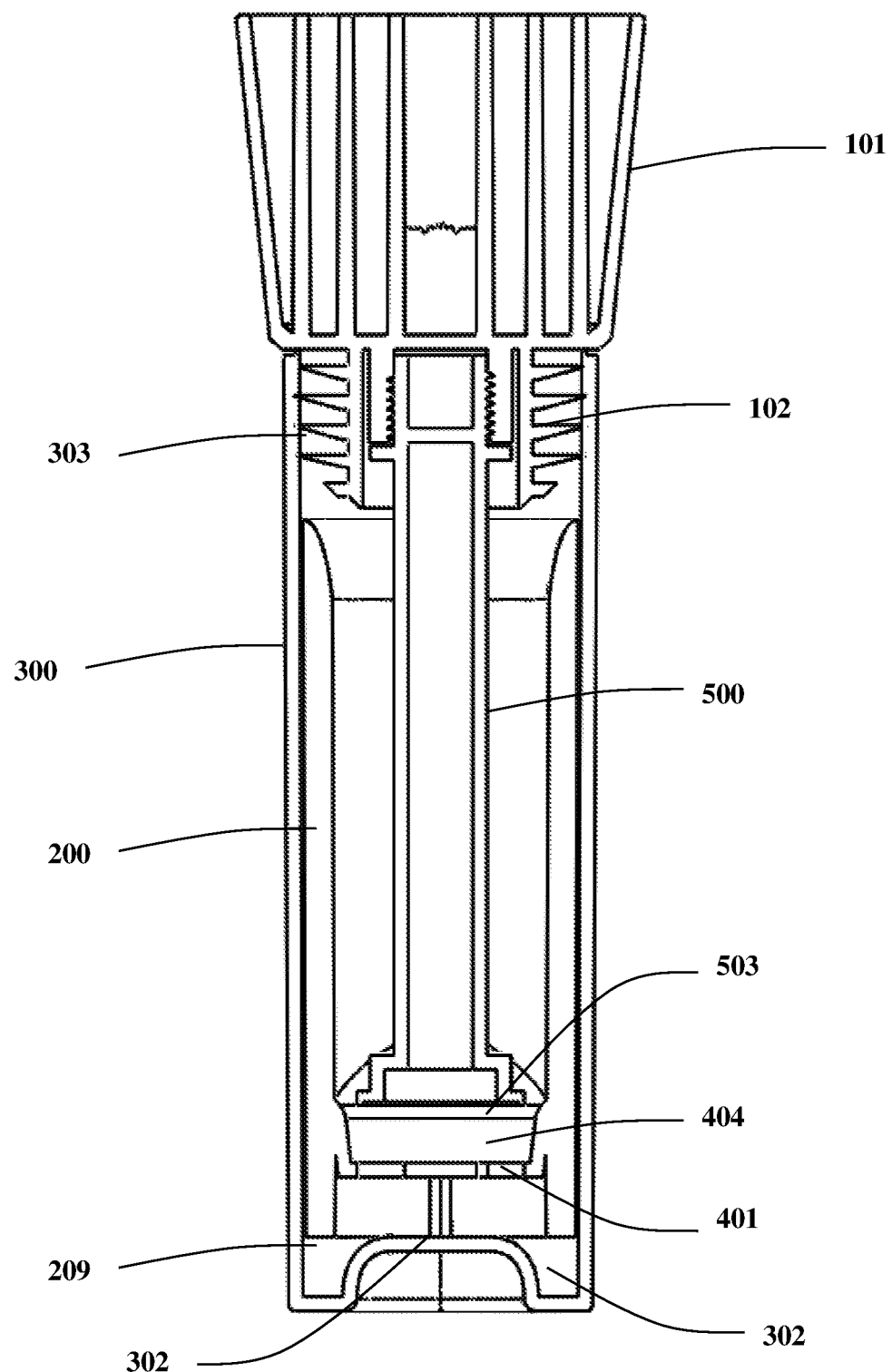
FIG. 8 is a schematic diagram showing the combined structure of the apparatus shown in FIG. 1 according to an embodiment of the present invention, showing the structure of extruded state of the absorbing element.

The present invention further provides a fluid sample collection element. In one embodiment, the fluid or liquid sample collection element comprises an absorbing element 503 and a gripping portion 100. The absorbing element 503 is generally made of a medical grade sponge or foam material commonly used in the art. However, the absorbing element can also be made of many other materials, such as cotton or paper, or any other material having water absorbing property. The gripping portion 101 is generally rigid, which can facilitate the operation of the absorbing element. The gripping portion 101 can be made of materials commonly used in the art, such as plastic, wood, metal or cardboard. In one embodiment, the gripping portion is connected to the absorbing element 503 through a rod structure 502, and one end of the rod structure is connected to the griping portion 101, and the other end including a wheel edge (see the FIG. 1 attached) and an absorbing element 503 are attached thereto. In some specific embodiments, the wheel edge comprises a sealing element, for example, a silicone elastomeric sealing ring (which may or may not be included), for sealing the absorbing element 503 into the receiving chamber 404 formed by the extrusion structure 400 of the carrier 200. In some embodiments, the gripping portion 100 comprises a holding portion 101 and a flexible sheet structure 102. The holding portion is used for collecting sample where the hand is held. By this way, the absorbing element 503 is conveniently placed in the mouth to collect the saliva sample. Thus, the volume of the holding portion is relatively large, facilitating to be held by hands without falling off. For example, as shown in FIG. 6 and FIG. 7, an annular elastic sheet 102 is provided on the extension of the holding portion 101. These loop and wing-like structures are flexible, when the holding portion with the absorbing element is inserted to the chamber 300, the elastic sheet structure 102 cooperates with the inner wall 303 of the chamber opening. Generally, the inner wall of the chamber opening is smooth without a threaded structure. The flexible sheet-like structure 102 cooperates with the inner wall, to form an opening-sealed state (FIG. 8). Since the flexible structure is in contact with the inner wall, the flexible structure deforms, such as flipping up, to achieve more close contact with the interior, thereby allowing the collection element to be retained in the chamber 300 and not easily detached from the chamber. In the following text, the advantages and effects of the flexible structure are described in details with the extrusion process of the absorbing element.

In some preferred embodiments, the gripping portion is connected to an inner plug or an inner plug is disposed on the gripping portion, while the flexible sheet-like structure is disposed on the inner plug, by this way, when the inner plug is inserted into the inner wall of the opening of the chamber 200, the flexible sheet structure is in contact with the inner wall, playing a role of sealing, in addition, retaining the absorbing element in the chamber or the extrusion chamber on the carrier. Actually, the process when the inner plug is inserted into the opening of the chamber 200 is the process in which the absorbing element is squeezed to release the collected liquid samples.

In order to better secure or bond the holding portion with the absorbing element to the inner wall 303 of the opening of the chamber 200, the flexible sheet structure may be a multi-layer structure, for example, as shown in FIG. 7, a five-layer structure. Of course, optionally, the maximum outer diameter of the flexible sheet-like structure is slightly larger than the diameter or inner diameter of the inner wall 303 of the chamber 200, by this way, when a flexible sheet-like structure with a wing shape is inserted into the inner wall of the chamber opening, the flexible structure has an upward flip, while the wing-shaped structure has a larger area to contact with the inner wall, so that it can form a seal, to allow the absorbing element to retain in the chamber 303. Therefore, in some embodiments, the sheet-like structure 103 can encircle the entire inner plug body 108, wrapping the flexible sheet-like structure 103 outwardly on the body. In some embodiments, the sheet-like structure has a triangular cross section, and the triangle is an acute triangle. Two sides 104 and 105 constitute the acute triangle, of which one side 104 is substantially vertical to the inner plug body 108, while the other side is inclined to the inner plug body. Thus, when the inner plug body is inserted into the chamber 300, the apex of the triangle is in contact with the inner wall, and as the insertion continues, part of the sheet-like structure is turned outwardly, so that the oblique side 105 is upward, and the longer oblique side 105 is in contact with the interior 303 of the chamber to form a sealed structure. Because the contact has a great friction, the absorbing element is retained in the chamber 303, forming a fixed structure.

In order to connect the absorbing element 503 with the griping portion 100, a threaded structure is provided in the inner plug body 108. The connecting rod 502 has a thread at one end and an absorbing element at the other end, thereby connected to the gripping portion in a thread way.

Testing Element Carrier

The carrier of the testing element of the present invention is the carrier 200 primarily used for carrying the testing element, comprising a body that accommodates the testing element. The body includes two surfaces: inner surface 208 and outer surface 205. A plurality of slots 201 are provided on the outer surface 205 of the body, and a testing element can be disposed or placed in the slot 201. In order to allow the testing element to be fixedly placed in the card slot 201 without detaching, two pairs of protrusions 2 are provided in the card slot 201, to maintain the testing element and prevent from detaching from the slot 201. In some embodiments, the sample absorption area of the testing element is exposed out of the body and extended from a section of opening 202 of the card slot 201, to directly contact with the fluid samples. In one embodiment, the exposed portion of the testing element is located in the collection area 302 of the chamber 300, to contact the liquid samples and form a liquid communication state.

In some embodiments, when the testing element is disposed in the slot 201, the surface 201 is covered with a transparent sheet, such as plastic, aluminum foil, adhesive sticker, etc., allowing the test strip in a dry environment or not to be affected by the external environment, for example, avoid accidental damage to the test strips during the assembly process. Of course, the sample absorption area of the test strip may not expose the opening of the card slot. Optionally, the outer surface of the carrier does not have any sheet covering the groove, but directly matches with the inner wall of the chamber. That is, the shape of the chamber is mutually adapted to the shape of the carrier, for example, the chamber is elliptical, then the carrier is also elliptical, such that the outer surface 205 of the carrier is in contact with the inner surface 308 of the chamber 300, allowing the inner surface 308 of the chamber to cover the slot 201 of the carrier 200.

Figure 5:
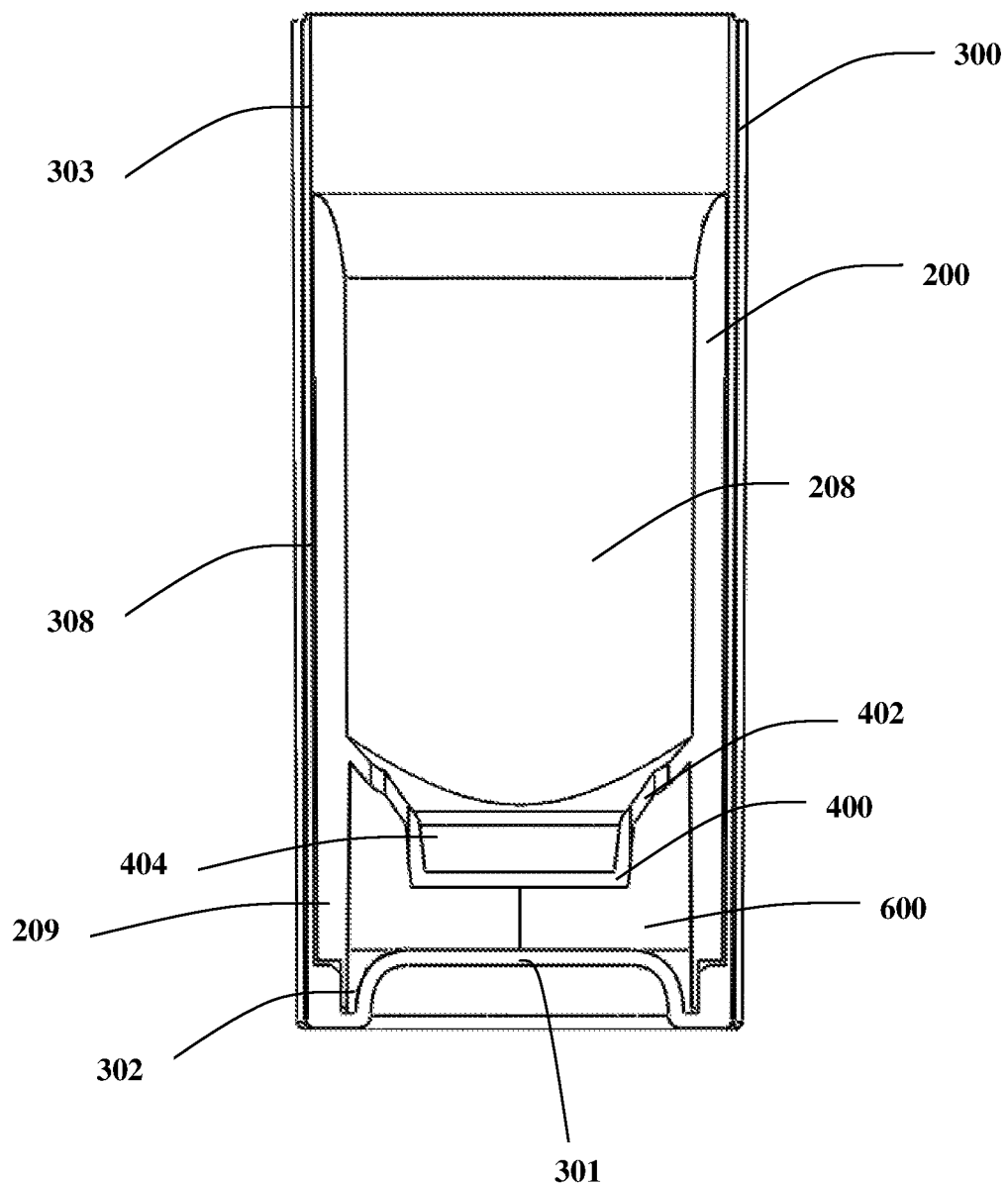
FIG. 5 is an assembled structural view of a carrier and a chamber accommodating a testing element according to an embodiment of the present invention.

Of course, it is also possible to prevent the outer surface 205 of the carrier from forming a tight fit with the inner surface 308 of the chamber, to facilitate assembly. Generally the carrier is one-slot injection molding. After completion, the testing element is disposed on the slot 201 of the outer surface of the carrier, allowing the sample applying area to slightly expose the opening 202 and extend out of the carrier. When the carrier with the testing element is placed in the chamber 300, the sample applying area of the testing element is placed in the collection area 302 at the bottom of the chamber 300 to contact the liquid samples (as shown in FIG. 5).

In some preferred embodiments, a structure for extruding the absorbing element, such as the structure 400, is also provided at the bottom of the carrier. The structure is also adapted to the shape of the carrier. For example, the shape of the carrier is elliptical, then the extrusion structure is also elliptical. One or more holes 401 are provided in the extrusion structure, and two holes 402 and 403 are also disposed at the junction of the extrusion structure and the carrier, so that the liquid samples released by absorbing element and extrusion structure due to compression will flow to the bottom of the chamber 300 through these holes, which will be collected in the collection area 302. The collection area 302 at the bottom of the chamber is formed by an area 301 that protrudes upwardly from the bottom of the chamber.

In some embodiments, the extrusion structure is a recessed chamber structure, with an extrusion chamber 404 having a plurality of holes 401 at the bottom thereof. There are one or more holes in the chamber connected to the carrier. For example, as shown in FIG. 5, when the absorbing element is received by the chamber structure and compressed, the liquid can flow into the chamber 300 that receives the carrier through the hole 401 at the bottom of the extrusion chamber 404, or flow into the chamber 300 that receives the carrier through the hole 402 at the side surface.

Figure 9:
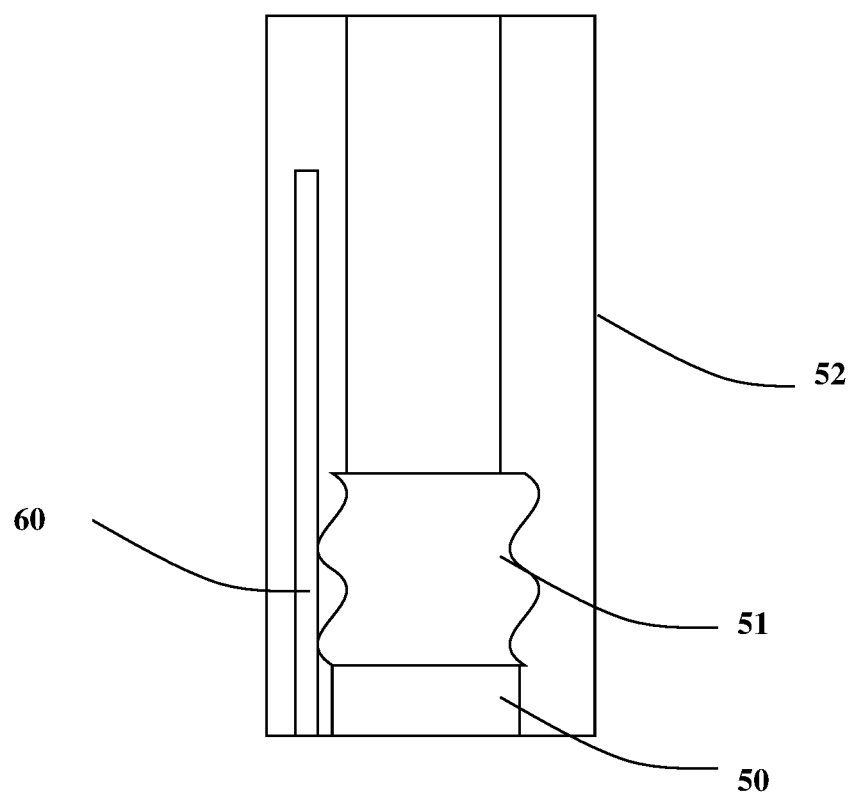
FIG. 9 is a schematic diagram showing defects in saliva extrusion and detection in comparison with conventional techniques.

Such a design has a number of advantages over existing conventional saliva collection apparatus. For example, as described in the U.S. Pat. No. 7,927,562, a protrusion structure 503 and a collection area 540 are provided at the bottom of the chamber receiving carrier as shown in FIGS. 1-6, allowing the absorbing element to contact with the protrusion structure 503 and squeezing the convex absorbing element to release the liquid samples. Actually, since the absorbing element 300 has a certain length, it usually becomes very soft after absorbing liquid samples, and actually there is a testing element 600 in the collection area 504, when the protrusion structure 503 is in contact with the absorbing element 300 absorbing the liquid samples, the absorbing element is not linearly compressed, but a phenomenon of bending and folding will occur. Such a bent and folded absorbing element will touch the test strip of the accessory or touch the sampling portion, thereby causing an increase in the local liquid amount. The liquid is not necessarily collected in the collection area 504 but adsorbed by the test strip directly. By this way, excessive liquid samples exist on some test strips, causing a flooding phenomenon, for example, as shown in FIG. 9, the liquid in other test strips will be reduced, thus, some test strips have excessive liquid, while some have very few liquid and unable to complete reactions, affecting the final detection results. In FIG. 9, 60 represents a test strip, and 51 represents an absorbing element (softened after absorbing liquid), 50 represents a protrusion, which contact with the absorbing element 60 to squeeze a liquid sample, and 52 represents a chamber. Moreover, the absorbing element is on the gripping portion 105, and the gripping portion is rotated and engaged with the chamber 506 by the thread, by this way, the absorption portion will also rotate, actually, it is rotated while compressed, such that the bent and folded absorbing element will contact with a number of testing elements. Moreover, sometimes the testing element is bent while the liquid is absorbed (becoming soft after absorbing liquid), or, as the absorbing element rotates, the sample applying areas of adjacent testing elements will be interleaved together, causing cross-reactions that affect the detection structure of the reagents. This is because the analytes corresponding to each test strip is different. In addition, the "test tube" as described in U.S. Pat. No. 7,927,562 is circular, which is inconvenient to take a picture or scan after the test.

The present invention overcomes these drawbacks. The structure that extrudes the absorbing element is moved away from the testing element, so the absorbing element will not touch any part of the testing element. Therefore, in some preferred embodiments, the structure 400 that extrudes the absorbing element or the extrusion chamber 404 that receives the absorbing element is away from the bottom of the chamber 300. Therefore, preferably, the carrier has a support structure 209, which surrounds the bottom space of the carrier, such that the bottom of the extrusion structure is located within the space 600 enclosed by the support structure, or the support structure surrounds the extrusion structure, as shown in FIG. 5. The extrusion structure 400 is inwardly recessed from the space 600 enclosed by the support structure, so that the test strip located in the groove on the carrier surface will not contact the absorbing element, thereby avoiding the flooding phenomenon. In addition, since the absorbing element 102 with the flexible sheet-like structure is in contact with the wall of the opening of the chamber 300 and it is a plug-in method without rotating, the absorbing element will not be rotated, thereby avoiding the contact between the absorbing element and the test strip or intersection of test strips.

In some specific embodiments of the present invention, the carrier of the testing element further comprises an extrusion chamber 404 that receive the absorbing element 503, the chamber includes the bottom of the chamber having one or more through-holes 401, such as four through-holes arranged symmetrically. The diameter of the through-hole 401 may be smaller than the diameter of the absorbing element 503. When the absorbing element contacts the bottom, it may be pressed by the acting force, so that the liquid samples absorbed on the absorbing element 503 are extruded, thereby flowing out via the through-hole 401. Preferably, the diameter of the through-hole 401 is substantially the same as the diameter of the absorbing element 503, and a hollow "cross" structure is disposed at the through-hole, by this way, when the absorbing element contacts the "hollow" structure at the bottom through-hole, it can be squeezed by the force, such that the liquid sample absorbed on the absorbing element 103 are extruded to flow into the bottom of the chamber 300 and collected in the collection area 302.

In some preferred embodiments, the chamber 404 and the carrier 200 receiving the testing element carrier are an integrated structure. Preferably, the chamber 4047 and the carrier 200 are one-shot injection molded. A card slot 201 is provided on the carrier 200.

Chamber that Accommodates the Testing Element Carrier

Figure 4:
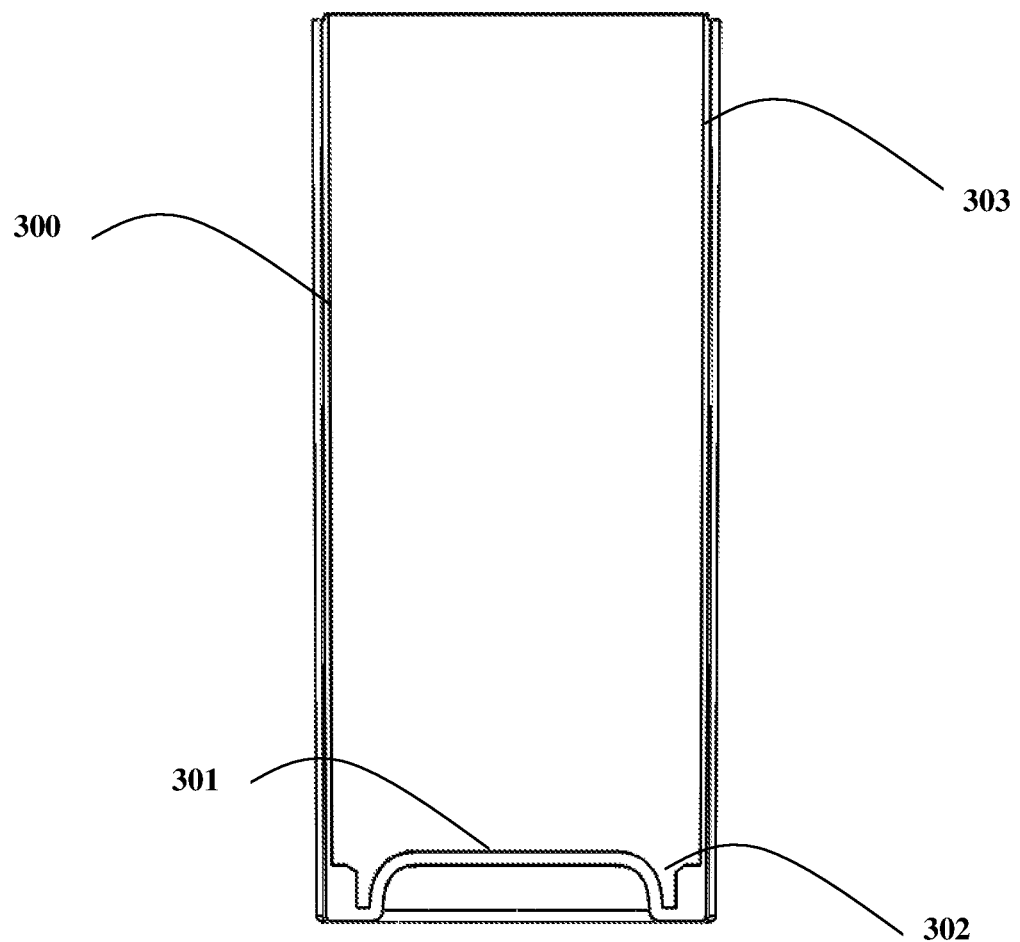
FIG. 4 is a schematic longitudinal sectional view of a chamber that accommodates a testing element carrier.

In a specific embodiment, the shape of the chamber 300 that accommodates the testing element carrier of the present invention is shown as in the FIG. 4. In addition to such structure, other appropriate structures may be provided. The chamber 300 that accommodates the testing element carrier is enclosed by an opening, a side wall and a bottom. The opening is used to allow the chamber that accommodates the testing element carrier 200 to enter the chamber 300. The height of the carrier 200 is less than that of the chamber. A support structure 209 is provided in the carrier, to form a structure relative to FIG. 5. A smooth inner wall 303 is provided at the opening. The smooth interior is connected with the flexible sheet-like structure 102 of the gripping portion, so that the flexible sheet-like structure is in contact with the inner wall, which plays a role of sealing and allows the collection element with an absorbing element to retain in the chamber. In contrast to the structure disclosed in U.S. Pat. No. 7,927,562, it is a thread structure, with thread on the chamber, therefore it increases the processing cost. In addition, the thread structure can only play a matching function, which is difficult to seal. When the test is completed and there are surplus liquid samples in the chamber, the liquid will leak from the thread joint to contaminate the external environment during the transportation. In the present invention, the flexible sealing sheet is in close contact with the inner wall of the chamber to provide a sealing effect and prevent the liquid in the chamber 300 from leakage. In fact, it is also unlikely that the structure of the plug is provided here. If the ring-shaped structure with the flexible sheet is removed and the flexible plug is used, the drawback is that, when the plug enters the chamber 300, the sealing effect is formed. However, since the opening of the chamber 300 is sealed, the plug is difficult to re-enter into the chamber 300 to compress the absorbing element 502 once sealed. Due to the sealed environment, the sealed gas is in the chamber, so a great force is required to allow the plug to enter the chamber 300. In the present invention, a multi-layer flexible sheet-like structure is adopted, which can form a seal by contacting the inner wall 303 of the smooth chamber along the edge of the sheet, thereby it is not difficult to form a liquid seal, and at the same time, the collection element with an absorbing element 503 is combined with the chamber 300 (as shown in FIG. 8).

In some embodiments, since the carrier 200 also form an inner chamber 208 in the chamber 300, the flexible sheet-like structure disposed on the inner plug body 108 does not have the same outer diameter, which may be different, for example, a first layer of flexible sheet-like structure 109 and a second layer and third layer of flexible sheet-like structure 107 are provided from bottom to top, but the outer diameter of the first layer of flexible sheet-like structure 109 is smaller than that of the second layer and third layer of flexible sheet-like structure. By this way, the first layer of flexible sheet-like structure 109 and the carrier form an inner wall of the chamber 208, that is, contact with the inner wall of the carrier, so that this part of flexible sheet-like structure is in contact with the inner wall of the chamber 200, and part is in contact with the inner wall 208 of the carrier, playing a role of double seal and double retention.

Here, the carrier is elliptical, and the chamber 200 is also elliptical. A plurality of grooves for accommodating the test strips is disposed on the two long sides of the elliptical carrier, when the detection is finished, the detection results can be obtained by scanning. The elliptical setting is more convenient for saving the results.

Detection Method

The detection method of analytes in the fluid samples is described in conjunction with the drawings.

A fluid collection element and an assembled detection apparatus are prepared. The detection apparatus comprises a chamber 300 that accommodates the testing element carrier and is located in a receiving element carrier 200 (as shown in FIGS. 1-6). Wherein, the fluid collection element comprises an absorbing element 503 that absorbs a fluid sample and a gripping portion 100 with a flexible sheet-like structure 102. The gripping portion 100 comprises a hand-held portion 101 and a plurality of ring-shaped flexible sheet-like structures 102 to connect 503 to the absorbing element through a connecting rod 502, thereby forming a specific fluid collection element. The absorbing element 503 is placed in the mouth for collecting saliva. When the entire absorption head is filled with saliva samples, the absorption head becomes soft. At this time, the collection element that absorbs the saliva samples is inserted into the chamber 300 that accommodates the testing element carrier through the opening. With the entering or inserting of the collection element, the liquid absorbing element enters the receiving cavity 404. At this time, as the flexible sheet layer of the inner plug body gradually enters the opening of the chamber 300, it cooperates with the inner wall. By this way, the absorbing element 503 is compressed in the extrusion chamber 404, thereby releasing the liquid samples to flow into the bottom of the chamber through the hole 401, and with further extrusion, the saliva retained in the absorbing element 103 is squeezed out, and the liquid samples released from the bottom of the absorbing element flow to the protrusion area through the through-hole 406, and the saliva samples are collected into the collection groove 302, while the liquid samples extruded from the upper portion of the absorbing element 503 flow through the hole 402 to the protrusion area, the saliva samples are collected into the collection groove 302, to contact with the absorption area of the testing element in the groove, so that the saliva samples rise along the testing element due to capillary action and flow to the detecting area, to perform detection of analytes.

When the collection element 10 is inserted into the chamber 300 that accommodates the testing element carrier, a plurality of flexible sheet-like structures 102 are in contact with the inner wall 303 at the opening of the chamber 300, achieving the sealing of the opening of the chamber 300. In addition, with the insertion, the absorbing element 503 is compressed, and the frictional force formed by the close contact between the flexible sealing sheet and the inner wall is sufficient to overcome the reaction force of the absorbing element when being compressed, thereby allowing the absorbing element and the entire collection to be retained on the chamber 300. When the detection is finished, the apparatus can be directly sent to a detection agency for second confirmatory detection when necessary. As the sealing of the flexible sealing sheet does not cause liquid leakage, when performing the secondary detection, the collection element 10 is taken out of the chamber 300 to collect the remaining liquid samples for secondary assay.

Example 1

150 saliva samples are collected from 150 subjects using the sample collection element described herein by placing the absorbing element 503 of the sample collection element in the subject's mouth until filled with saliva. After samples are collected, the sample collector is placed in the extrusion chamber 404 of the apparatus that accommodates the testing element carrier 200 to compress the absorbing element 503, and extrude samples and then directly detected. The 50 negative samples are mixed with a mixture of drugs of abuse, including amphetamine, cocaine, methamphetamine, opiates, THC, and phencyclidine. The same procedures are performed using the absorbing element 503 to collect liquid. 10 minutes later, the results are recorded as positive or negative. Three test strips are placed on each carrier 200, and each test strip can test three kinds of drugs of abuse. The following six drugs of abuse are detected by the three test strips: amphetamine (AMP), cocaine (COC), methamphetamine (MET), opiates (OPI), tetra-hydrocannabinol (THC) and phenylcyclohexylpiperidine (PCP).

The 100 samples without drugs of abuse are tested negative, with a compliance rate of 100%. For each of the six drugs, positive results are provided for 50 samples that have been spiked with the drug mixture, with a compliance rate of 100%.

Similarly, the same test is carried out using the apparatus described in U.S. Pat. No. 7,827,562, and it is found that no results are obtained in 15 of 100 negative samples. When the absorbing element is extruded, excessive liquid is absorbed by the test strip, to cause the flooding, so the compliance rate is only 85%. In the 50 samples that are confirmed of positive, positive results are obtained in only 35 samples, and the remaining samples (15 samples) are abandoned because the adjacent test strips are overlapped and no accurate results are obtained, and the compliance rate is only 70%.

Example 2—Detection Sensitivity Experiment

This embodiment is intended to illustrate the detection sensitivity of the apparatus and method in the present invention. Each sample solution is detected with ten apparatuses, for a total of 300 tests. Saliva samples are used for detection for these apparatuses. The test strips used have antigens of the detected drugs. The test strips use a competition method, with antibodies labeled with colloidal gold in the labeled area and antigen on the test line.

The apparatus is also detected by cocaine (COC), methylamphetamine (MAMP), phencyclidine (PCP), tetrahydrocannabinol (THC), morphine (MOP) or amphetamine (AMP) PBS solution, which contain 0, 0.5, 1.5 and 3 times of the limit of detection. For example, the limit of detection of THC in saliva is 4 ng/ml. Therefore, the PBS solutions containing THC of 0 ng/ml, 2 ng/ml, 6 ng/ml and 8 ng/ml are detected. The amount of the tested drugs is shown in the following table.

When detection is performed, the foregoing mentioned negative saliva, PBS, or spiked PBS are absorbed by the absorption sponge of the sample collector, and then extruded into the absorption head and receiving chamber for testing. The liquid is allowed to enter the groove 206 to contact the test strips by the capillary action. The test results are recorded and shown in the table below 10 minutes later.

| Drug (Limit of Detection) | Saliva | PBS | PBS + 0.5X drug | PBS + 1.5X drug | PBS + 3X drug |
|---|---|---|---|---|---|
| COC (20 ng/ml) | 0 ng/ml | 0 ng/ml | 10 ng/ml | 30 ng/ml | 60 ng/ml |
| MAMP (50 ng/ml) | 0 ng/ml | 0 ng/ml | 25 ng/ml | 75 ng/ml | 150 ng/ml |
| PCP (10 ng/ml) | 0 ng/ml | 0 ng/ml | 5 ng/ml | 15 ng/ml | 30 ng/ml |
| THC (4 ng/ml) | 0 ng/ml | 0 ng/ml | 2 ng/ml | 6 ng/ml | 12 ng/ml |
| MOP (40 ng/ml) | 0 ng/ml | 0 ng/ml | 20 ng/ml | 60 ng/ml | 120 ng/ml |
| AMP (50 ng/ml) | 0 ng/ml | 0 ng/ml | 25 ng/ml | 75 ng/ml | 150 ng/ml |

The above results show that the prevent invention can obtain a good sensitivity.

The invention shown and described herein may be implemented in the absence of any elements, limitations specifically disclosed herein. The terms and expressions used herein are for illustration rather than limitation, which do not exclude any equivalents of the features and portions described herein in the use of these terms and expressions, in addition, it should be understood that various modifications are feasible within the scope of the present invention. It is therefore to be understood that, although the invention has been particularly disclosed by various embodiments and alternative features, modifications and variations of the concepts described herein may be employed by those of skilled in the art, and such modifications and variations will fall into the scope of protection of the present invention as defined by the appended claims.

The contents of the articles, patents, patent applications, and all other documents and electronic information available or documented herein are incorporated herein by reference in their entirety, as if each individual publication is specifically and individually indicated for reference. The applicant reserves the right to incorporate any and all materials and information from any such article, patent, patent application or other document into this application.

The invention claimed is:

1. An apparatus for collecting and detecting an analyte in a fluid sample, comprising:
   a fluid sample collection element comprising:
      an absorbing element;
      a carrier for accommodating a testing element, the carrier comprising an extrusion structure that is in contact with the absorbing element and extrudes the absorbing element;
   a chamber for accommodating the carrier, wherein the carrier is located in the chamber; and
      one or more flexible sheet-like structures, wherein through the engagement of said one or more flexible sheet-like structures with the inner wall of the chamber, the sealing of the chamber by said one or more flexible sheet-like structures and the extrusion of the absorbing element is achieved, and wherein said one or more flexible sheet-like structures has an acute triangle section that includes two long sides, one of the long sides being perpendicular to an inner plug body and the other long side being substantially inclined with the inner plug body.

2. The apparatus according to claim 1, wherein the absorbing element is extruded by the extrusion structure to release liquid samples during the engagement of the collection element with the chamber.

3. The apparatus according to claim 1, wherein the flexible sheet-like structure is located on the inner plug body.

4. The apparatus according to claim 1, wherein the long side perpendicular to the inner plug is located above the long side inclined with the inner plug body.

5. The apparatus according to claim 4, wherein the outer diameter formed by the flexible sheet-like structure is greater than the inner diameter of the inner wall of the chamber.

6. The apparatus according to claim 1, wherein the extrusion structure and the carrier structure are an integrated structure or a one-shot injection molded structure.

7. The apparatus according to claim 6, wherein the carrier comprises an inner surface and an outer surface, and the outer surface has one or more grooves for accommodating the testing element.

8. The apparatus according to claim 7, wherein a testing element is disposed in the slot, a sampling applying area of the testing element extends outwardly from the opening of the slot, so that part of the sampling applying area is located at the bottom of the chamber.

9. The apparatus according to claim 8, wherein a protrusion area is provided in the chamber, and the protrusion area and the inner wall of the chamber form a liquid collection area.

10. The apparatus according to claim 9, wherein a part of the sample applying area is located at the collection area to contact with the liquid samples in the collection area.

11. The apparatus according to claim 1, wherein the carrier comprises a support structure and the support structure forms a space, and the extrusion structure is located in the space.

12. The apparatus according to claim 11, wherein the extrusion structure comprises an extrusion chamber, and one or more through-holes are provided at the bottom of the extrusion chamber, liquid samples extruded from the absorbing element flow to the bottom of the chamber through the through-holes.

13. The apparatus according to claim 12, wherein one or more through-holes are included in the junction of the extrusion chamber with the inner surface of the carrier, and liquid samples extruded from the absorbing element flow to the bottom of the chamber via the through-hole.

14. An apparatus for collecting and detecting an analyte in a fluid sample, comprising:
   a fluid sample collection element comprising:
      an absorbing element that absorbs fluid samples;
      a gripping portion that has an inner plug body, the inner plug body comprising a flexible sealing sheet-like structure; and
      a connecting rod that connects the absorbing element and the gripping portion;
   a testing element carrier, wherein the testing element carrier comprises a body for carrying a testing element and an extrusion structure for contacting the absorbing element and extruding the absorbing element; and
   a chamber for accommodating the carrier therein, which has an opening and inner wall, wherein the flexible sealing sheet-like structure cooperates with the inner wall of the chamber, thereby forming an opening for sealing the chamber, and allowing the fluid sample collection element to be retained in the chamber that accommodates the testing element carrier, and wherein the flexible sealing sheet-like structure has an acute triangle section, the acute triangle including two long sides, wherein one of the long sides is perpendicular to the inner plug body, and the other of the long sides is substantially inclined with the inner plug body, wherein the long side that is perpendicular to the inner plug body is located above the long side that is inclined with the inner plug body.

15. The apparatus according to claim 14, wherein the inner plug is connected to the gripping portion.

* * * * *